United States Patent [19]

Lueders et al.

[11] Patent Number: 4,473,369
[45] Date of Patent: Sep. 25, 1984

[54] CONTINUOUS AMBULATORY PERITONEAL DIALYSIS CLAMPING SYSTEM

[75] Inventors: Arthur Lueders, Mundelein; Marc Bellotti, Winnetka; James Fitzgerald; Larry C. Taylor, both of McHenry, all of Ill.

[73] Assignee: Baxter Travenol Laboratories, Inc., Deerfield, Ill.

[21] Appl. No.: 338,712

[22] Filed: Jan. 11, 1982

[51] Int. Cl.³ ............................................. A61M 5/14
[52] U.S. Cl. .................................. 604/244; 604/29; 604/283; 604/411; 604/250; 604/905
[58] Field of Search ................ 604/905, 29, 244, 283, 604/411; 128/346; 251/7

[56] References Cited

U.S. PATENT DOCUMENTS

| 2,889,848 | 6/1959 | Redmer | 251/7 X |
|---|---|---|---|
| 3,106,415 | 10/1963 | Breunich | 287/91 |
| 3,685,795 | 8/1972 | Caster | 604/244 X |
| 3,902,489 | 9/1975 | Carter | 604/905 X |
| 4,056,116 | 11/1977 | Carter et al. | 137/68 R |
| 4,080,965 | 3/1978 | Philips | 604/905 X |
| 4,340,052 | 7/1982 | Dennehey et al. | 128/247 |

Primary Examiner—Stephen C. Pellegrino
Attorney, Agent, or Firm—Paul C. Flattery; Garrettson Ellis

[57] ABSTRACT

A system is provided for connection of a transfer spike on the end of a tube with another tube, in which the connection portions may be ultraviolet sterilized prior to connection. Both the spike and the tube for connection communicate with a housing member having a tubular, collapsible sheath member which is ultraviolet transparent. Also, a clamping system may be provided for closing flow through the system.

39 Claims, 8 Drawing Figures

CONTINUOUS AMBULATORY PERITONEAL DIALYSIS CLAMPING SYSTEM

BACKGROUND OF THE INVENTION

This invention relates to a connector system, and more particularly, to a system for use in peritoneal dialysis generally.

Specifically, continuous ambulatory peritoneal dialysis (CAPD) is an increasingly popular form of dialysis. CAPD employs a bag of sterile peritoneal dialysis solution which is opened through a pierceable membrane. The bag is connected to a patient's peritoneal cavity through a tubing set which includes a membrane-piercing spike. In order to perform dialysis, fresh solution in the bag is drained into the peritoneal cavity and remains in the cavity for the dialysis or dwell period, usually four to six hours. At the end of that period, spent dialysis solution is drained from the cavity back to the bag. Then a second bag of fresh solution is exchanged for the bag of spent solution, is connected to the tubing set, and the cavity is filled with fresh solution and the dialysis process repeated.

One of the principal areas of concern in peritoneal dialysis generally is that the connection between the tubing set and the dialysis solution bag must be kept sterile, particularly when the bag membrane is pierced in order to drain the solution from the bag to fill the peritoneal cavity.

Ultraviolet (UV) sterilization is a desirable form of sterilization for use in a peritoneal dialysis procedure, particularly CAPD.

It is an object of this invention to provide such a connector which can be UV-sterilized and easily used by a patient.

This and other objects will become apparent from the following description and appended claims.

SUMMARY OF INVENTION

In accordance with this invention a connector system is provided for use in peritoneal dialysis, and particularly CAPD applications, to connect the patient's catheter to a supply of dialysis solution through a tubing set having a transfer spike and catheter coupler.

The connector may comprise an ultraviolet transparent, longitudinally expansible and collapsible housing member which can receive the transfer spike at one end and which receives a tube from a solution container at the other end. Clamp means are also provided to permit closing of flow through the solution container tube. When the housing member is in its extended position, the spike is spaced from a pierceable sealing membrane within the tube of the solution container. When the housing member is in its collapsed position, the spike penetrates the tube of the solution container.

A casing may also be provided to retain the spike and bag tubing in either its position spaced from the pierceable membrane or its position in which it extends through the pierceable membrane.

At least portions of the housing member are desirably ultraviolet transparent, so that after connection of the spike and the tubing within the housing member, but before penetration of the pierceable membrane, the interior of the housing member can be sterilized by application of ultraviolet light from the exterior.

More specifically, the housing member includes a tubular, collapsible sheath member having a collapsible tubular, ultraviolet-transparent, spike-receiving section with a spike-receiving opening on one end, and an integral housing portion at the other end of the spike-receiving section.

The housing portion has a tube-receiving opening aligned with the spike-receiving section for receiving a dialysis solution bag delivery tube typically closed with a pierceable membrane. The housing portion also has a transverse slide clamp-receiving slot.

A slide clamp is associated with the housing portion slot, the clamp having a tube-grasping slot, and being carried and movable within the housing slot between tube closing and tube opening positions, referring to the dialysis solution bag delivery tube.

As the result of this, the dialysis solution bag delivery tube may be inserted into the sheath through the housing end, and held in a piercing position by moving the slide clamp to the closing position. The transverse spike may be inserted into the sheath at the other end and held for application of ultraviolet light. After the ultraviolet application, for antibacterial effect within the sheath, the spike is thrust into the dialysis solution bag delivery tube to pierce the membrane which closes it, to provide a sterile connection between the spike and the tube so that the liquid can flow between the solution container and the peritoneal cavity of a patient.

The casing member which retains the transfer spike either in piercing or nonpiercing position may comprise a pair of hinged halves having grooves at each end which are proportioned to grasp clamping shoulders or flanges positioned at opposed ends of the collapsible sheath member, to hold the sheath member in an open position, or alternatively to grasp one end of the collapsible sheath member and a flange or clamping shoulder on the spike, to hold the system in collapsed, membrane-piercing relation.

Other details of the invention are as shown in the drawings and specification below.

DESCRIPTION OF THE PREFERRED EMBODIMENT

Figures 1, 2:
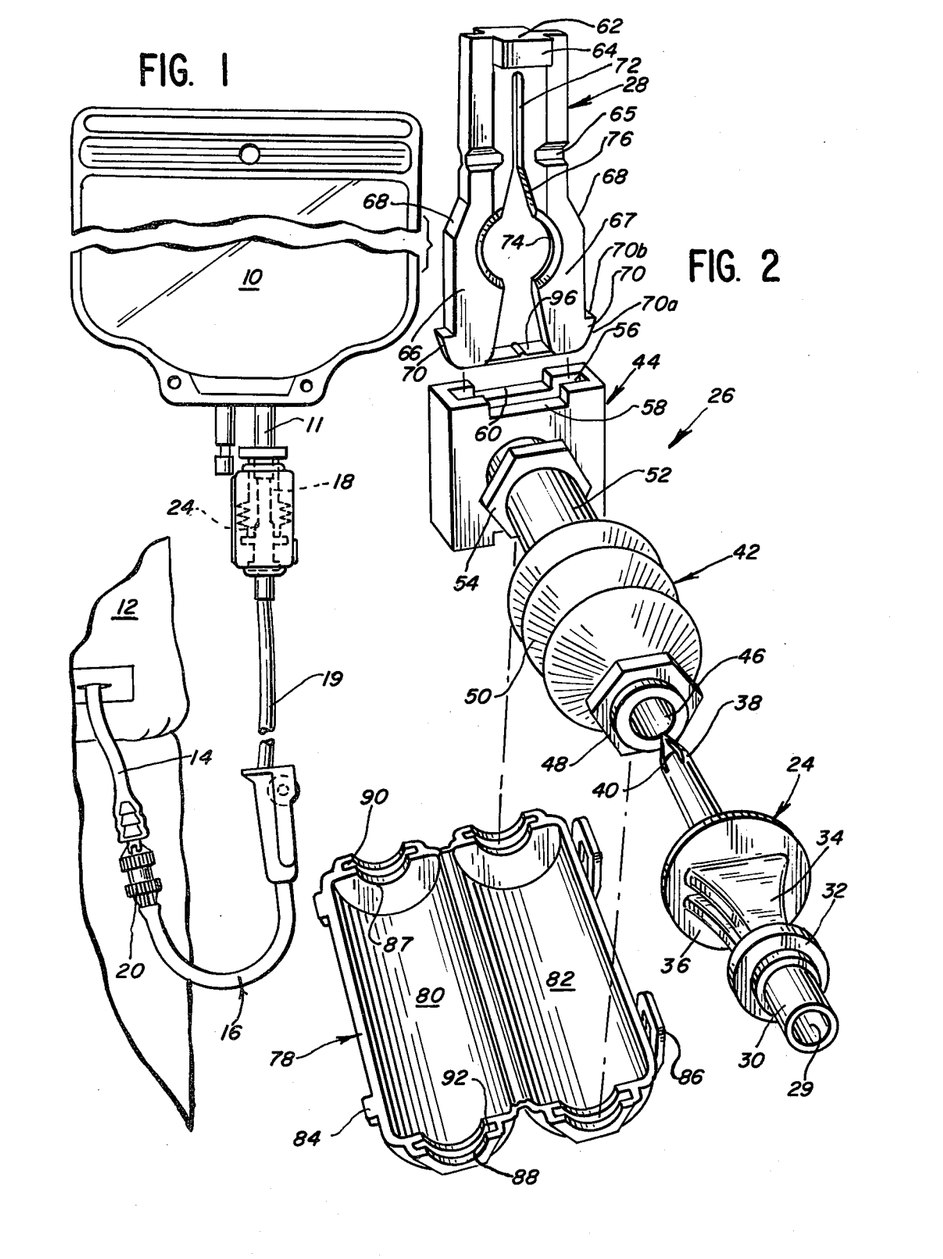
FIG. 1 is a diagrammatic view showing the solution bag, the connector, the tubing set, the catheter, and the patient.
FIG. 2 is an exploded perspective view showing the spike and the connector of FIG. 1.

Referring now to FIG. 1, peritoneal dialysis solution bag 10 which has a short delivery tube 11, is shown coupled to a patient 12 through catheter 14, tubing set 16, and connector 18. The tubing set 16, which is replaced perhaps once a month, includes a length of tubing 19, a catheter coupler 20 for connecting the tube set to the catheter, and a transfer spike 24. If so desired, a filter may be included in the tubing set.

The transfer spike 24 and connector system 18, which includes sheath and housing member 26 and slide clamp 28, are shown in FIG. 2. Spike member 24 has a central bore 29, a tubing set connecting end 30, a round clamping shoulder 32; a handle or grasping center section 34 which includes a round disc-like member 36; and a hollow piercing or spiking point 38 having liquid flow ports 40 which communicate with bore 29.

The sheath and housing member 26 includes a hollow spike-receiving sheath member 42, and a slide-receiving housing 44. The spike-receiving section 42 is hollow and tubular, having an accordion-like shape, and is collapsible. Section 42 includes a spike-receiving aperture 46, hexagonal clamping shoulder 48, and convoluted, collapsible, ultraviolet transparent section 50. Second tubular section 52 and second hexagonally-shaped clamping shoulder 54 are also provided. Collapsible section 50 may be made of an ultraviolet transparent plastic such as polyethylene or other desired plastic, preferably selected and formed so that at least 15 percent of the ultraviolet radiation to which it is exposed passes into its interior for sterilization therein.

Figures 3, 4, 5, 6:
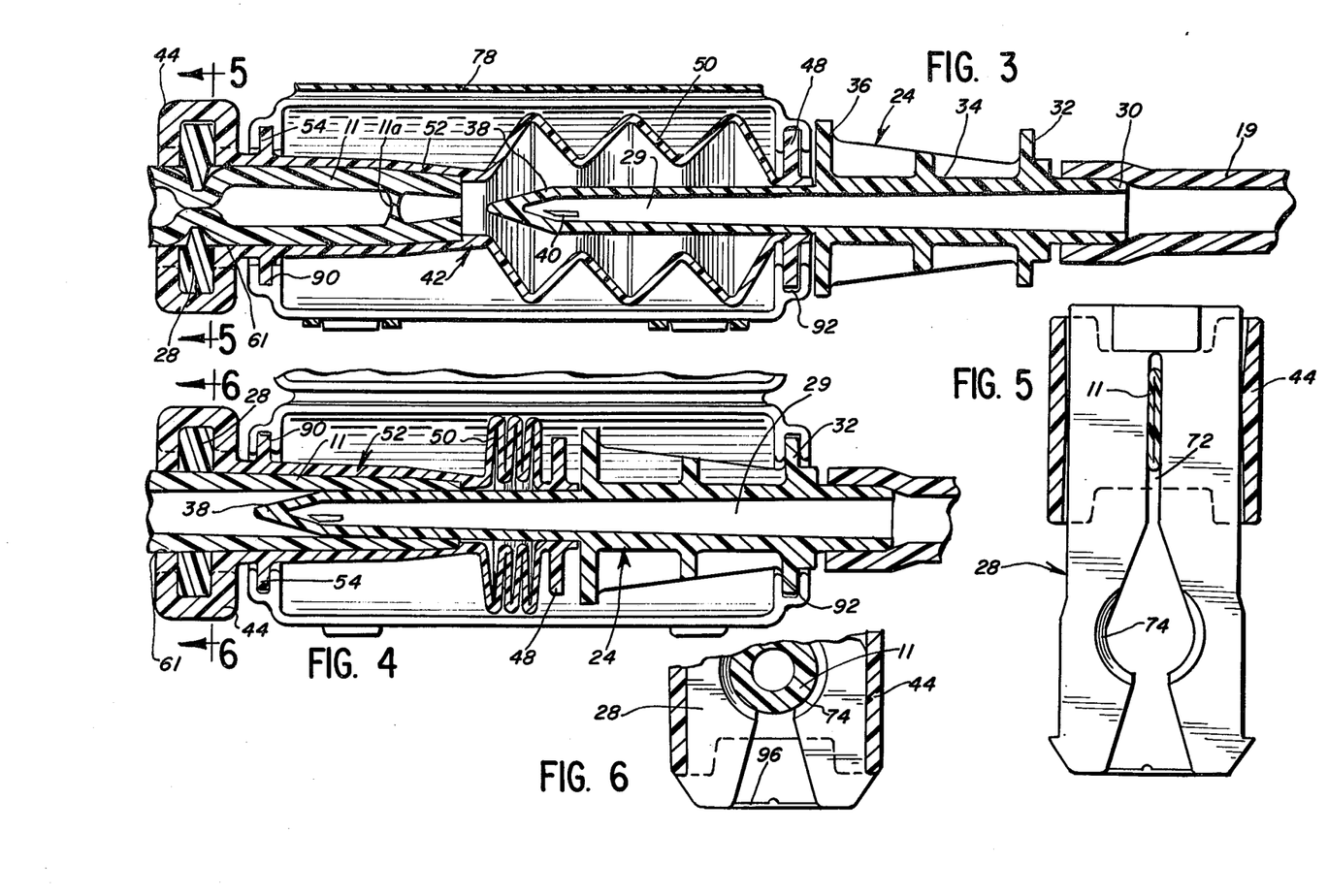
FIG. 3 is a sectional view showing the connector with the spike of FIG. 1 in the non-piercing sterilization position.
FIG. 4 is a sectional view similar to FIG. 3 showing the connector with the spike in the pierced position.
FIG. 5 is a sectional view taken along line 5—5 of FIG. 3 and showing the slide clamp grasping the tube end.
FIG. 6 is a fragmentary transverse sectional view taken along line 6—6 showing the slide clamp in the non-grasping position.

Slide housing 44 may be integral with sheath member 42, being connected thereto adjacent to clamping shoulder 54. Housing 44 may be rectangularly shaped, having a transversely oriented slide-receiving slot 56 extending through its central portion, and a pair of stepped stop ledges 58, 60. Slide clamp 28 is preferably insertable into slide housing 44 from either end of slot 56, with leg 67 on either the right or left side of slot 56. Housing 44 includes a delivery tube-receiving opening 61 which is aligned with tubular member 52 and is best seen in FIG. 4.

Slide member 28 is a bifurcated, fork-like member having a bight or head section 62 that includes a downward movement-limiting shoulders 64 which cooperate with the stops 58, 60 in limiting the movement of the slide member relative to the housing. A pair of mirror image shaped legs 66, 67 extend from the head section 62. The outer surface of each leg 66 and 67 includes outwardly tapering, shoulder-like intermediate portions 68, and limit shoulder hooks 70 for limiting upward movement of the slide clamp. The legs 66, 67 are shaped so as to form a thin slot 72 extending from head section 62 downwardly toward an enlarged tube-receiving opening 74. A tapered tube-guiding section 76 connects slot 72 and enlarged opening 74. It will be noted that the shoulder portions 68 are positioned slightly above opening 74, and this provides some spring bias to the slide clamp so as to maintain its position in the housing when the slide is in an upper position where limit shoulders 70 engage the slide housing.

Each of limit shoulders or hooks 70 may define tapering ramp section 70a which permits insertion of the slide into slot 56. Hooks 70 can engage the lower edges of the housing 44 so as to limit upward movement of the slide clamp. Hooks 70 also can provide alignment of opening 74 with housing aperture 61 and sheath tube 52 when they engage the lower edges of housing 44.

A "clamshell" retention casing 78 is provided for positioning spike 24 relative to clamp 28. Casing 78 has two hingedly-connected half sections 80, 82 which may be substantially identical, except that section 80 includes tongue-like members 84 and section 82 includes latch-like members 86 for locking cooperation with members 84. Each section includes end wall formations 87, 88, that define grooves 90, 92, which can receive hexagonally-shaped clamping shoulders 48, 54 on the sheath, and round shoulder 32 on the spike to immovably retain the system in connected relation.

Referring now to FIG. 3, a spike member 24 is shown in a non-piercing sterilization position. As can be seen, casing 78 is shown holding the collapsible portion 50 of the sheath in an expanded position, with shoulders 48, 54 being held in grooves 92 and 90 of the casing 78, respectively. With this arrangement, piercing spike 24 can be inserted into the sheath, but it cannot pierce the delivery-tube membrane 11a that prevents flow through tube 11 of bag 10, which is inserted into tube 52 at one end. Tube 11 is shown being held in position by slide clamp 28, which has been pressed downwardly so as to grasp and close tube 11 in slot 72. As shown in FIG. 3, pierceable membrane 11a is still sealed. The piercing or transfer spike 24 is inserted into sheath member 50, but by virtue of the casing 78 it is prevented from piercing the membrane 11a.

FIG. 5 shows tubing clamp 28 holding tubing 11 in the grasping position shown in FIG. 3.

After connection of the parts, clamshell casing 78 can be removed, and sheath section 42, carrying tube end 11, membrane 11a, and spike 24 may be placed in an ultraviolet sterilizer. After appropriate sterilization with ultraviolet light, spike 24 is then thrust through membrane 11a so as to pierce the membrane, to permit fluid flow from bag 10 through spike 24 and from there to the patient.

Referring now to FIG. 4, hollow point 38 of spike 24 is shown thrust through membrane 11a, and slide clamp 28 is then raised to the non-grasping, flow permitting position shown in FIG. 6.

Once spike 24 has been thrust through membrane 11a, casing 78 is then reapplied to hexagonal shoulder 54, and round shoulder 32 on spike 24 as in FIG. 4. This holds the spike in a fluid flow position so that fresh solution can flow from the bag through the spike to the patient with hollow point 38 holding tubing 11 in position by friction. After the peritoneal cavity is filled, clamp 28 is moved to its sealing, grasping position to close off tube 11. Casing 78 can remain attached and clamp 28 can remain in closed position throughout the dwell period of the dialysis solution in the peritoneal cavity until it is time to drain the cavity of spent solution and to exchange solution bags.

Figures 7, 8:
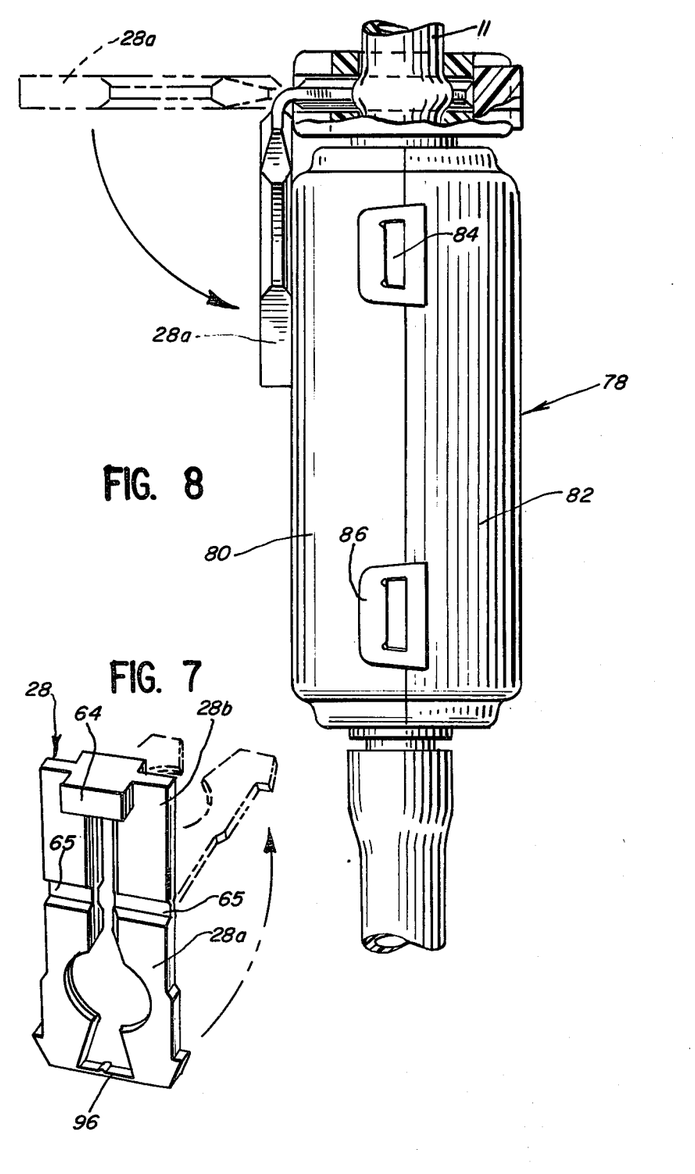
FIG. 7 is a perspective view of the slide clamp showing notch-like surface recesses for folding of the upper clamp section relative to the lower clamp section.
FIG. 8 is a side elevational view of the clamp in the folded position with the "clamshell" retainer in position.

Referring now to FIGS. 7 and 8, slide clamp 28 includes a pair of transverse lines of folding weakness 65 which permit folding of the clamp to minimize its size and facilitate its concealment by the patient during use. As seen in FIG. 7, the lower section 28a of clamp 28 may be folded transversely along the fold lines 65 to a position at right angle with the upper section 28b. The folding relative to clampshell casing 78 is shown in FIG. 8, with section 28a being bent over toward casing 78, and with tube 11 in closed, no-flow position. This folding feature may be used in the solution dwell portion of dialysis.

Integral flexible strap 96 on clamp 28 limits the spreading of legs 66, 67 to assure the sealing of tube 11 when placed in slot 72. In operation, slide clamp 28 is inserted into slide housing 44 by aligning clamp 28 with housing slot 56 and then pushing clamp 28 downwardly.

The clamp entrance ramps 70a engage the edges of slot 56 to bias the clamp legs inwardly and permit them to enter the housing. Clamp 28 is pushed downwardly until the hooks 70 emerge from the other end of the slot 56, and legs 66 and 67 then snap outwardly and engage the inside walls of the slot. Hooks 70, in cooperation with the housing provide an upward movement limiting means with clamp opening 74 being aligned with sheath opening 61.

In use, delivery tube 11 of a bag 10 is inserted into housing 44, and clamp 28 is then pushed downwardly to grasp and close tube 11 in slot 72. The downward movement of clamp 28 is limited by the engagement of clamp shoulders 64 with housing ledges 58, 60. Next, casing 78 may be applied to flanges 48, 54 and spike 24 may then be inserted into sheath 42. The spike, sheath and tube end are then sterilized by ultraviolet radiation after preferably removing casing 78. During ultraviolet sterilization, spike 24 remains spaced from membrane 11a so that the sterile seal has not been pierced.

After sterilization, the spike 24 is grasped in one hand, housing 44 is grasped in the other hand, and the spike is thrust into tube 11 to puncture membrane 11a. Thereafter casing 78 is positioned about the sheath and spike so as to grasp shoulders 32 and 54, to hold spike 24 in the piercing position.

Then, clamp 28 is retracted to its open position, so that dialysis solution can flow from bag 10 to the patient. After bag 10 is emptied, clamp 28 is thrust downward to again grasp and close tube 11, to close the bag during dialysis solution dwell.

During the dwell phase with solution residing in the peritoneal cavity, the bag and connector may be carried by the patient about his waist. In order to minimize bulk, clamp 28 can be folded about the fold lines as seen in FIGS. 7 and 8.

When it is necessary to drain the peritoneal cavity, clamp 28 is folded open and slid outwardly so that spent dialysis solution can be drained from the cavity into bag 10. Thereafter, a bag of fresh solution can be exchanged for the bag of spent solution, and the above procedure repeated.

Spike 24 and especially hollow piercing point 38 are preferably made of an ultraviolet-transparent material to permit antimicrobial effect within bore or lumen 29 upon irradiation by a source of ultraviolet light, for example poly(methylpentene), a polyolefin such as polyethylene or polypropylene, EEA(poly(ethylene-ethyl acetate)) or poly(chlorotrifluoroethylene).

Sheath and housing member 26 may be made as a separate item from bag 10 and spike 24, and may be made of a polyolefin such as polyethylene, or other flexible, ultraviolet transparent material such as EEA. Thus the sheath and housing member may be used with different formulations of peritoneal dialysis solution and types of bags, for example. Also, sheath and housing member 26 may be used with currently available bags of peritoneal dialysis solution.

When shoulders 48, 54 are polygonal in shape, and slots 90, 92 in casing 78 are of matching polygonal shape, casing 78 grips member 26 in fixed manner, preventing relative rotation therebetween. This facilitates the installation and removal of tube 11 of container 10 into and from the system, and protects bellows 50.

The above has been offered for illustrative purposes only, and is not intended to limit the scope of the invention of this application, which is as defined in the claims below.

That which is claimed is:

1. A connector system for use in peritoneal dialysis applications and the like to connect a patient's catheter to the delivery tube of a supply of dialysis solution through a tube set having a transfer spike and catheter coupler, said connector system comprising:

a housing member which includes a tube-like, collapsible sheath member having a collapsible tubular, ultraviolet-transparent, spike-receiving section with a spike-receiving opening at one end, and an integral housing portion at the other end of the spike-receiving section, said housing member also having first and second shoulder formations for carrying means for alternatively retaining a transfer spike in piercing and non-piercing positions relative to a pierceable membrane of the delivery tube installed in said housing member, the first shoulder formation being adjacent the spike-receiving opening and the second shoulder formation being adjacent the housing portion, said housing portion having a tube-receiving opening aligned with said spike-receiving section for receiving said delivery tube closed with the pierceable membrane, and also a transverse slide clamp-receiving slot said slot extending through said housing so as to provide slide clamp-receiving openings at either end; and a slide clamp cooperatively associated with said housing portion in said clamp-receiving slot, said clamp defining a tube-grasping slot, and being carried and movable within said housing slot between tube-closing and tube opening positions;

whereby the delivery tube may be inserted into said sheath member through said housing end and held in a piercing position by moving said slide clamp to said closing position, and a transfer spike may be inserted into said sheath member at the other end held for ultraviolet treatment, and then thrust into said tube end to pierce the membrane associated therewith and provide a sterile condition.

2. A connector system as in claim 1, in which said means for alternatively retaining a transfer spike in piercing and non-piercing positions relative to the supply of dialysis solution and pierceable membrane is present.

3. A connector system as in claim 2, in which said alternatively retaining means includes:

removable retention casing means having a pair of spaced shoulder-grasping ends fixedly spaced from one another, said ends being adapted to grasp the first and second shoulder formations on the housing member so as to prevent collapsing of the spike-receiving section upon insertion of the spike into the sheath.

4. A connector system as in claim 3, wherein a transfer spike may also be held in piercing position by the retention casing means wherein the retention casing means grasps the first shoulder formation on the sheath member adjacent the housing portion and a third shoulder formation on the transfer spike after advancement of the spike through the membrane.

5. A system as in claim 1, wherein said slide clamp is a member having a head section and two leg sections, and said leg sections define between them a tube-grasping slot adjacent the head section and a tube-receiving opening more remote from said head section.

6. A system as in claim 5, wherein said slide clamp includes a pair of outwardly-extending hook-like stop members at the end of said leg opposite the head section, said hook-like members being adapted to engage the housing sections so as to provide a movement limiting stop.

7. A system as in claim 6, wherein each of said hook-like members include tapering ramp portions at the ends thereof for cooperation with said housing slot in guiding said slide clamp into said housing slot.

8. A system as in claim 5, wherein said clamp includes transverse folding grooves intermediate with the head section and distal end for permitting said clamp to be folded about said lines.

9. A system as in claim 5, wherein the outer surface of each of said slide member legs includes an outwardly tapered portion intermediate with the slide housing slot so as to bias the slide clamp outwardly against the housing and to cooperate in maintaining the clamp in a nongrasping position within said housing.

10. A system as in claim 1, wherein the tube set includes a length of medical tubing, catheter coupling means at one end for connecting the tube set to a patient's catheter, and said membrane-piercing transfer spike connected to the other end of said tubing.

11. A system as in claim 10, in combination with a bag of dialysis solution, said bag having a delivery tube, said tube having a pierceable membrane for cooperation with said sheath member and slide clamp for piercing by said transfer spike.

12. The connector system of claim 10 in which said transfer spike is transparent to ultraviolet light.

13. The connector system of claim 12 in which said transfer spike is made of poly(methylpentene).

14. A system as in claim 1, wherein said slide clamp has a head section, two leg sections and a closed foot section, and said leg sections define between them a tube-grasping slot adjacent the head section and a tube-receiving opening more remote from said head section than said foot section.

15. A connector system for use in peritoneal dialysis applications and the like to connect a patient's catheter to the delivery tube of a supply of dialysis solution through a tube set having a transfer spike and a catheter coupler at opposite ends thereof;
said connector comprising a housing member which includes a tube-like, collapsible sheath member having a hollow, accordion-like ultraviolet transparent spike-receiving section having a spike-receiving-opening at one end of said section and an integral housing section at the other end of said spike-receiving-section, said sheath member also having a pair of shoulder formations, the first shoulder formation being adjacent the spike-receiving opening and the second shoulder formation being adjacent the housing, said housing section having a tube-receiving-opening aligned with the spike-receiving section for receiving said delivery tube, and a transverse slide clamp-receiving slot, said slot extending through said housing so as to provide slide clamp-receiving openings at either end;
a slide clamp cooperatively associated with said slot, said clamp having a tube grasping slot and being movable within said housing slot between tube closing and tube opening positions;
removable retention casing means having a pair of spaced, shoulder-grasping ends fixedly spaced from one another, said ends being proportioned to grasp said pair of shoulder formations for positioning said transfer spike in a spaced position relative to a pierceable membrane in said delivery tube positioned in said opening by preventing collapsing of said sheath member;
whereby said delivery tube may be inserted into said sheath through said housing end and held in a piercing position by moving said slide clamp to said grasping position and whereby said transfer spike may be inserted into said sheath at the other end and retained in spaced relation from the pierceable membrane and thereafter thrust toward said tube so as to pierce the membrane associated therewith after removal of the retention casing means.

16. The connector system of claim 15 in which said spaced first and second shoulder formations are of a shape to prevent relative rotation of said tube-like collapsible sheath member with respect to the retention casing means.

17. The connector member of claim 16 in which said retention casing means is proportioned to grasp the first shoulder formation on the sheath member adjacent said housing portion and a third shoulder formation on the transverse spike after advancement of the spike member.

18. A connector system for use in peritoneal dialysis applications and the like to connect a patient's catheter to a supply of dialysis solution through a tube set having a transfer spike and catheter coupler, said connection system comprising:
a housing member which includes a tubular, collapsible sheath member having a collapsible tubular ultraviolet-transparent, spike-receiving section with a spike-receiving opening at one end, an integral housing portion at the other end of the spike-receiving section, said housing portion having a tube-receiving opening aligned with said spike-receiving section for receiving a dialysis solution container delivery tube closed with a pierceable membrane, and also a transverse, clamp-receiving slot;
a slide clamp cooperatively associated with said housing portion in said slot, said clamp defining a tube-grasping slot and carried and movable within said housing slot between delivery tube closing and delivery tube opening positions;
casing means provided for alternatively retaining a transfer spike in piercing and nonpiercing positions relative to the anticipated position of the pierceable membrane, said casing means defining slots at opposed ends thereof, and a pair of first and second shoulder formations defined on the spike-receiving, collapsible sheath member whereby said shoulder formations can fit into the slots of the casing to prevent collapse of the sheath member, and said delivery tube may be inserted into said sheath member through the tube-receiving opening and held in position by moving said slide clamp to said closing position, and also a transfer spike may be inserted into said sheath member at the other end and held spaced from the tube end for ultraviolet treatment, and then thrust into said tube end to pierce the membrane associated therewith.

19. The connector system of claim 18 in which said transfer spike carries a third shoulder formation adapted for fitting in an end slot of said casing, whereby the collapsible, tubular, spike-receiving section may be held in collapsed position with one slot of the casing engaging the first shoulder formation and the other slot of the casing engaging the third shoulder formation of the transfer spike.

20. The connector system of claim 19 in which said slide clamp defines a pair of leg sections connected at one end to a head section, said leg sections defining between them a grasping slot into which the delivery tube of the solution container can be placed to close said tube and to grasp it, said slot also defining a tube-receiving opening more remote from the head section than said grasping slot through which the delivery tube can extend in a manner permitting fluid flow therethrough.

21. The connector system of claim 20 in which said casing comprises a pair of casing halves connected together in hinged relation.

22. The connector system of claim 19 in which said transfer spike is transparent to ultraviolet light.

23. The connector system of claim 3 in which said spaced first and second shoulder formations are of a shape to prevent relative rotation of said tube-like collapsible sheath member with respect to the retention casing means.

24. The connector system of claim 23 in which said retention casing means is proportioned to grasp the first shoulder formation on the sheath member adjacent said housing portion and a third shoulder formation on the transverse spike after advancement of the spike member.

25. A connector system for use in peritoneal dialysis applications and the like to connect a patient's catheter to the delivery tube of a supply of dialysis solution through a tube set having a transfer spike and catheter coupler, said connector system comprising:
   a housing member which includes a tubular, ultraviolet-transparent, spike-receiving section with a spike-receiving opening at one end, and an integral housing portion at the other end of the spike-receiving section, said housing portion having a tube-receiving opening aligned with said spike-receiving section for receiving said delivery tube closed with a pierceable membrane, and also a transverse slide clamp-receiving slot; and,
   a slide clamp cooperatively associated with said housing portion in said slot, said slide clamp having a head section and two leg sections, and said leg sections defining between them a tube-grasping slot adjacent the head section and a tube-receiving opening more remote from said head section than the slot, said slide clamp further including a pair of outwardly-extending hook-like stop members at the ends of said legs opposite the head section, said hook-like members being adapted to engage the housing section so as to provide a movement limiting stop;
   whereby the delivery tube may be inserted into said tubular section through said housing end and held in a piercing position by moving said slide clamp to said closing position, and a transfer spike may be inserted into said spike-receiving section at the other end held for ultraviolet treatment, and then thrust into said tube end to pierce the membrane associated therewith and provide a sterile condition.

26. A system as in claim 25, wherein said tubular, spike-receiving section includes a longitudinally collapsible portion, and said slide clamp has a closed foot section, said hook-like stop members being adjacent the foot section.

27. A connector system for use in peritoneal dialysis applications and the like to connect a patient's catheter to the delivery tube of a supply of dialysis solution through a tube set having a transfer spike, said connector system comprising:
   a housing member which includes a tube-like member having a tubular, ultraviolet-transparent, spike-receiving section with a spike-receiving opening at one end, and an integral housing portion at the other end of the spike-receiving section, said housing portion having a delivery tube-receiving opening aligned with said spike-receiving section for receiving said delivery tube closed with a pierceable membrane, and also a transverse slide clamp-receiving slot; and,
   a slide clamp cooperatively associated with said housing portion in said slot, said clamp defining a tube-grasping slot, and being carried and movable within said housing slot between tube-closing and tube-opening positions, said slide clamp having a head section and two leg sections, and said leg sections defining between them said tube-grasping slot adjacent the head section and a tube-receiving opening more remote from said head section than said tube-grasping slot, wherein the outer surface of said slide member leg sections includes an outwardly-tapered portion adjacent the tube-receiving opening to bias the slide clamp against the housing when in contact therewith for frictionally maintaining the clamp out of tube-closing position within said housing;
   whereby the delivery tube may be inserted into said tubular section through said housing end and held in a piercing position by moving said slide clamp to said tube-closing position, and a transfer spike may be inserted into said sheath member at the other end, held for ultraviolet treatment, and then thrust into said delivery tube to pierce the membrane associated therewith and provide a sterile connector.

28. A system as in claim 27, wherein said tubular spike-receiving section includes a collapsible portion, and said slide clamp has a closed foot section, said tube-receiving opening being more remote from said head section than said foot section, said hook-like stop members being at the ends of said legs opposite the head section, adjacent the foot section.

29. A connector system for use in peritoneal dialysis applications and the like to connect a patient's catheter to the delivery tube of a supply of dialysis solution through a tube set having a transfer spike, said connector system comprising:
   a housing member which includes an ultraviolet-transparent, spike-receiving tubular section, with a spike-receiving opening at one end and an integral housing portion at the other end of the spike-receiving tubular section, said tubular section carrying shoulder formation means to be gripped by means for retaining the connector system, said housing portion having a tube-receiving opening aligned with said spike-receiving tubular section for receiving said delivery tube closed with a pierceable membrane, and also a transverse, slide clamp-receiving slot extending through said housing so as to provide slide clamp-receiving openings at either end;
   a slide clamp cooperatively associated with said housing portion in said clamp-receiving slot, said clamp defining a tube-grasping slot, and being carried and movable within said clamp-receiving slot between tube-closing and tube opening positions;

whereby the delivery tube may be inserted into said tubular section through said tube-receiving opening and held in a piercing position by moving said slide clamp to said closing position, and a transfer spike may be inserted into said tubular section at the other end held for ultraviolet treatment, and then thrust into said tube end to pierce the membrane associated therewith and provide a sterile condition.

30. The connector system of claim 29 in which at least a portion of said tubular ultraviolet-transparent, spike-receiving tubular section is inwardly tapered.

31. The connector system of claim 30 in which said tubular section defines an inner stop member to limit advance of said delivery tube therein.

32. A connector system for use in peritoneal dialysis applications and the like to connect a patient's catheter to the delivery tube of a supply of dialysis solution through a tube set having a transfer spike, said connector system comprising:

a housing member which includes an ultraviolet-transparent, spike-receiving tubular section with a spike-receiving opening at one end and an integral housing portion at the other end of the spike-receiving tubular section, said tubular section carrying shoulder formation means to be gripped by means for retaining the connector system, said housing portion having a tube-receiving opening aligned with said spike-receiving tubular section for receiving said delivery tube closed with a pierceable membrane, and also a transverse, slide clamp-receiving slot extending through said housing portion so as to provide slide clamp-receiving openings at either end;

a slide clamp cooperatively associated with said housing portion in said clamp-receiving slot, said slide clamp defining a tube-grasping slot, and being carried and movable within said clamp-receiving slot between tube-closing and tube-opening positions;

the slide clamp defining a tube-receiving opening for retaining said delivery tube in the tube-opening position, outer surfaces of said slide member defining an outwardly tapered portion adjacent said tube-receiving opening to bias the slide clamp against said housing when in engagement with said housing portion for frictionally maintaining the slide clamp in tube-opening position within said housing portion;

whereby the delivery tube may be inserted into said tubular section through said tube-receiving opening and held in a piercing position by moving said slide clamp to said closing position, and a transfer spike may be inserted into said tubular section at the other end held for ultraviolet treatment, and then thrust into said tube end to pierce the membrane associated therewith and provide a sterile condition.

33. The system of claim 32 wherein said slide clamp includes transverse folding grooves spaced from the ends thereof for permitting said clamp to be folded about said lines.

34. The system of claim 33 in which at least a portion of said tubular section is inwardly tapered.

35. The system of claim 34 which carries hook-like stop member means at the end of said slide clamp opposite said head section.

36. The system of claim 35 in which said shoulder formation means defines a shape to prevent relative rotation thereof in retained position.

37. The system of claim 35 in which said tubular spike-receiving member defines an inner stop member to limit advance of said delivery tube therein.

38. A connector system for use in peritoneal dialysis applications and the like to connect a patient's catheter to the delivery tube of a supply of dialysis solution through a tube set having a transfer spike, said connector system comprising:

a housing member which includes an ultraviolet-transparent, spike-receiving tubular section with a spike-receiving opening at one end and an integral housing portion at the other end of the spike-receiving tubular section, said tubular section carrying shoulder formation means to be gripped by means for retaining the connector system, said housing portion having a tube-receiving opening aligned with said spike-receiving tubular section for receiving said delivery tube closed with a pierceable membrane, and also a transverse slide clamp-receiving slot extending through said housing portion so as to provide slide clamp-receiving openings at either end;

a slide clamp cooperatively associated with said housing portion in said clamp-receiving slot, said slide clamp defining a tube-grasping slot, and being carried and movable within said clamp-receiving slot between tube-closing and tube-opening positions, at least a portion of said tubular section being inwardly tapered and defining an inner stop member to limit advance of said delivery tube therein; whereby the delivery tube may be inserted into said tubular section through said tube-receiving opening and held in a piercing position by moving said slide clamp to said closing position, and a transfer spike may be inserted into said tubular section at the other end held for ultraviolet treatment, and then thrust into said tube ends to pierce the membrane associated therewith and provide a sterile connection.

39. The system of claim 38 in which said shoulder formation means defines a shape to prevent relative rotation thereof in retained position.

* * * * *

UNITED STATES PATENT AND TRADEMARK OFFICE
CERTIFICATE OF CORRECTION

PATENT NO. : 4,473,369
DATED : September 25, 1984
INVENTOR(S) : Arthur Lueders, et al It is certified that error appears in the above-identified patent and that said Letters Patent is hereby corrected as shown below:

The term of this patent subsequent to January 25, 2001, has been disclaimed.

Signed and Sealed this

Third Day of September 1985

[SEAL]

Attest:

DONALD J. QUIGG

*Attesting Officer*     *Acting Commissioner of Patents and Trademarks - Designate*